United States Patent

Baldwin et al.

[11] Patent Number: 5,235,059
[45] Date of Patent: Aug. 10, 1993

[54] TRICYCLIC THIENOTHIOPYRAN CARBONIC ANHYDRASE INHIBITORS

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 782,866

[22] Filed: Oct. 15, 1991

[51] Int. Cl.$^5$ .................. A61K 31/54; A61K 31/445; C07D 513/12
[52] U.S. Cl. ................................. 514/291; 514/912; 546/80
[58] Field of Search ................ 546/83, 80; 514/291

[56] References Cited

U.S. PATENT DOCUMENTS 4,619,939  10/1986  Maren .
4,677,115   6/1987  Baldwin et al. .
4,797,413   1/1989  Baldwin et al. ................... 514/432

Primary Examiner—C. Warren Ivy
Assistant Examiner—D. Margaret Mach
Attorney, Agent, or Firm—William H. Nicholson; Joseph F. DiPrima

[57] ABSTRACT

Conformationally constrained tricyclic thienothiopyran compounds are topically effective carbonic anhydrase inhibitors useful in the treatment of ocular hypertension and glaucoma associated therewith.

5 Claims, No Drawings

TRICYCLIC THIENOTHIOPYRAN CARBONIC ANHYDRASE INHIBITORS

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many opthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. Many of these agents, however, also have other characteristics, e.g. membrane stabilizing activity, that are not acceptable for chronic ocular use. (S)-1-tert-Butylamino[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. Benzothiophene-2-sulfonamides, benzenesulfonylthiophene-2-sulfonamides, and thieno[2,3-b]thiopyran-2-sulfonamides are also reported to be carbonic anhydrase inhibitors topically effective in reducing intraocular pressure in U.S. Pat. Nos. 4,668,697; 4,585,787; and 4,797,413, respectively.

U.S. Pat. No. 4,619,939 discloses a process and composition for reducing intraocular pressure and reducing aqueous humor formation by applying topically to the cornea an effective amount of an aqueous solution of a carbonic anhydrase inhibitor having the following properties:

a. sufficiently soluble in water to form at least a 3 mM solution at pH 8.2 or a pKa of not greater than 7.3;
b. ether partition coefficient of at least 1.0;
c. chloroform partition coefficient of at least 0.01;
d. dissociation constant against carbonic anhydrase of not more than $3 \times 10^{-8}$ molar;
e. first order rate constant for penetration of the sulfonamide through a living rabbit cornea of at least 0.005 $hr^{-1}$;
f. not injurious to the cornea; and
g. stable in aqueous solution and in contact with the cornea.

OBJECTS OF THE INVENTION

It is an object of the present invention to provide compounds that are effective in treating ocular hypertension and glaucoma associated therewith by topical ocular administration. This and other objects of the present invention will be apparent from the following description.

SUMMARY OF THE INVENTION

This invention relates to conformationally constrained tricyclic thienothiopyrans of the structural formula

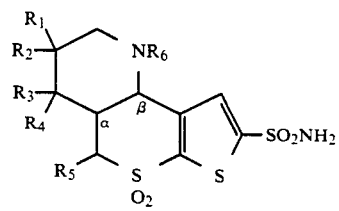

having a cis configuration at the $\alpha$- and $\beta$-carbons, the enantiomers and mixtures thereof, or an ophthalmologically acceptable salt thereof wherein $R_1$, $R_2$, $R_3$, $R_4$, and $R_6$ are independently H or straight or branched chain lower alkyl; $R_5$ is H, lower alkyl, lower alkenyl or lower alkyl substituted by hydroxy, alkoxy, hydroxyalkoxy, alkoxyalkoxy, hydroxyalkoxyalkoxy, alkylamino, hydroxyalkylamino, alkoxyalkylamino, hydroxyalkoxyalkylamino, alkyl-S(O)$_m$, hydroxyalkyl-S(O)$_m$, alkoxyalkyl-S(O)$_m$, hydroxyalkoxyalkyl-S(O)$_m$, alkyl-S(O)$_m$alkyoxy, hydroxyalkyl-S(O)$_m$alkyoxy, alkyl-S(O)$_m$alkyl-S(O)$_m$ and hydroxyalkyl-S(O)$_m$alkyl-S(O)$_m$.

DETAILED DESCRIPTION OF THE INVENTION

The novel compounds prepared according to the present invention have the structural formula

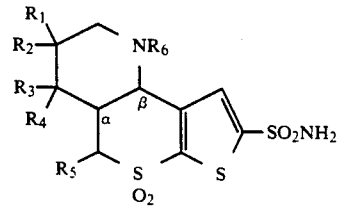

having a cis configuration at the $\alpha$- and $\beta$-carbons, the enantiomers and mixtures thereof or an opthalmologically acceptable salt thereof wherein:

$R_1$, $R_2$, $R_3$, $R_4$, and $R_6$ are H or straight or branched chain $C_{1-6}$alkyl, $R_5$ is
1) H or lower alkyl, preferably $C_{1-6}$;
2) $C_{1-6}$ alkyl substituted with
   a) hydroxy,
   b) $C_{1-3}$alkyl—O—,
   c) hydroxy$C_{1-3}$alkyl—O—,
   d) $C_{1-3}$alkyl—O—$C_{1-3}$alkyl—O—,
   e) hydroxy$C_{1-3}$alkyl—O—$C_{1-3}$alkyl—O—,
   f) $C_{1-3}$alkyl—NH—,
   g) hydroxy$C_{1-3}$alkyl—NH—,
   h) $C_{1-3}$alkyl—O—$C_{1-3}$alkyl—NH—,
   i) hydroxy$C_{1-3}$alkyl—O—$C_{1-3}$alkyl—NH—,
   j) $C_{1-3}$alkyl—S(O)$_m$—,
   k) hydroxy$C_{1-3}$alkyl—S(O)$_m$—,
   l) $C_{1-3}$alkyl—O—$C_{1-3}$alkyl—S(O)$_m$—,
   m) hydroxy$C_{1-3}$alkyl—O—$C_{1-3}$alkyl—S(O)$_m$—,
   n) $C_{1-3}$alkyl—S(O)$_m$—$C_{1-3}$alkyl—O—,
   o) hydroxy$C_{1-3}$alkyl—S(O)$_m$—$C_{1-3}$alkyl—O—,
   p) $C_{1-3}$alkyl—S(O)$_m$—$C_{1-3}$alkyl—S(O)$_m$,
   q) hydroxy$C_{1-3}$alkyl—S(O)$_m$—$C_{1-3}$alkyl—S(O)$_m$—,
3) $C_{2-6}$alkenyl;
and m is independently 0, 1 or 2.

Preferred compounds of the present invention are those wherein $R_1$, $R_2$, $R_3$, $R_4$, and $R_6$ are independently H or $C_{1-6}$alkyl, and $R_5$ is H, $C_{1-6}$alkyl or $C_{1-6}$alkyl substituted by hydroxy, alkoxy, hydroxyalkoxy, alkoxyalkoxy, alkylamino, alkoxyalkylamino, alkyl—S(O)$_m$—, hydroxy—$C_{1-3}$alkyl—S(O)$_m$ $C_{1-3}$alkyl—S(O)$_m$—$C_{1-3}$alkyl—S(O)$_m$—, $C_{1-3}$alkyl—O—$C_{1-3}$alkyl—S(O)$_m$—, $C_{1-3}$alkyl—S(O)$_m$—$C_{1-3}$alkyl—O—, or $C_{2-6}$alkenyl, and m is independently 0, 1 or 2.

The compounds of the present invention are prepared by reacting 2-methylene-4-ethoxycarbonylbutyric acid, or an $R_1$, $R_2$, $R_3$, $R_4$-substituted derivative thereof with 2-mercaptothiophene. The reaction is carried out in triethylamine at reflux temperature for a period of from 2 to about 36 hours after which the reaction mixture is cooled and poured into mineral acid, preferably HCl. The aqueous layer is extracted with a polar solvent such as, for example, ethyl acetate (EtOAc), and the organic extracts are backwashed with saturated NaCl. The dried extracts are conveniently purified by chromatography to yield the product of formula 1.

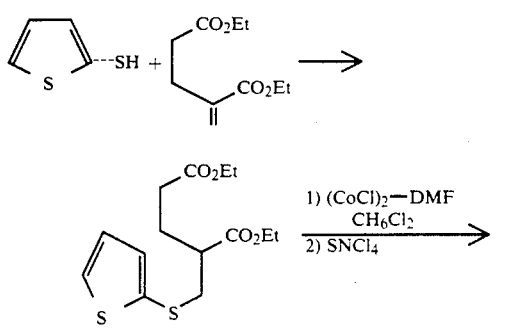

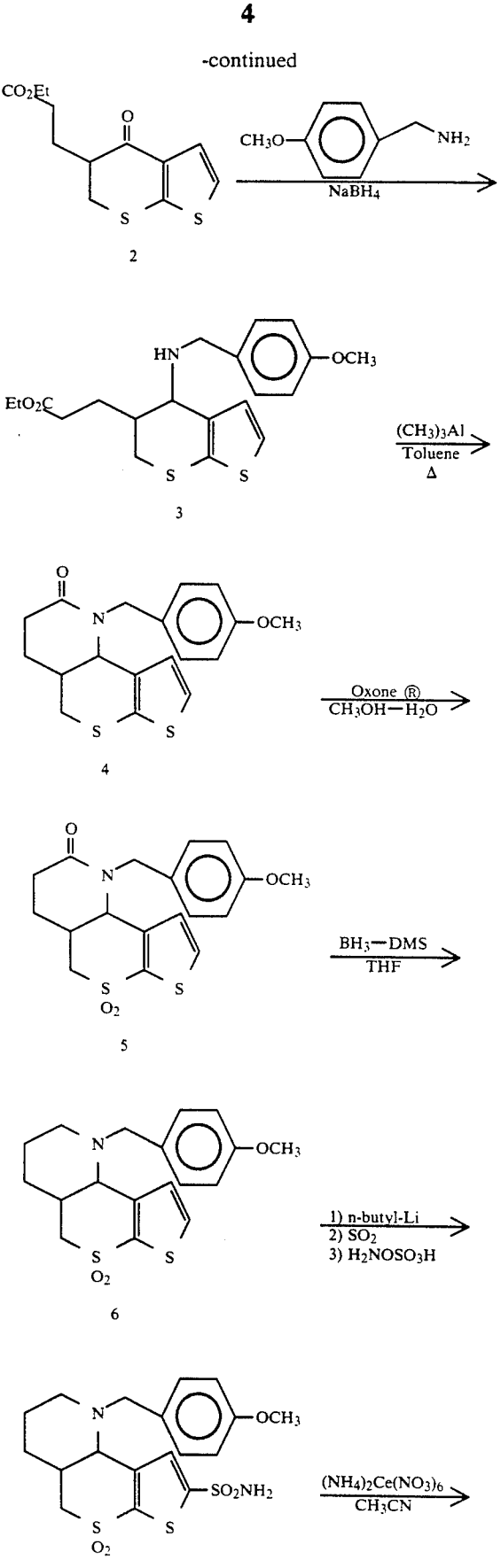

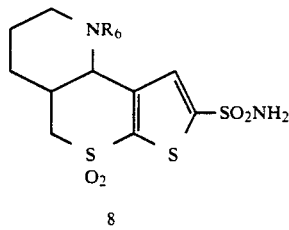

8

Thionyl chloride is added to the product of formula 1 in a polar solvent such as, for example methylene chloride with mixing for a period of from about 1 hour to about 10 hours. The mixture is then cooled and SnCl$_4$ is added with stirring for an extended period of from about 10 to about 40 hours. The mixture then is added to water and the aqueous layer extracted with a polar solvent such as, for example, EtOAc. The organic extracts are backwashed with saturated NaHCO$_3$, dried, filtered and concentrated to dryness to yield the compound of formula 2.

To a solution of compound 2 in polar solvent such as, for example, a mixture of tetrahydrofuran (THF) and toluene, there is added 4-methoxybenzylamine. Titanium tetrachloride is added and the resulting mixture is stirred for from a few minutes to about 4 hours, preferably from about 0.5 hour to about 2 hours, then added to a cold stirred suspension of NaBH$_4$ in an alkanol, preferably ethanol. The resulting mixture is stirred for from a few minutes to about 4 hours, preferably from about 0.5 hour to about 2 hours, and acidified to pH 1 with mineral acid, preferably HCl. The solvent is removed, preferably in vacuo and the residue is partioned between EtOAc and saturated NaHCO$_3$ solution. The EtOAc layer is separated, dried and concentrated to dryness to yield the compound of formula 3.

A solution of (CH$_3$)$_3$Al in a polar solvent, preferably toluene, is added to a stirred solution of compound 3 at lowered temperature, preferably about 0° under an inert atmosphere. The reaction mixture is brought to ambient temperature, heated at reflux for about 1 hour to about 6 hours, then cooled to about 0° and then treated with mineral acid, preferably HCl. It is diluted with H$_2$O and EtOAc. The layers are separated and the organic phase is washed with H$_2$O, brine, dried and concentrated to dryness to yield the compound of formula 4.

A solution of Oxone ® is added to a stirred solution of the compound of formula 4. After stirring for from about 0.5 hour to about 4 hours, the reaction mixture is extracted with a polar solvent such as, for example, EtOAc. The organic layer is washed with aqueous sodium bisulfite solution, brine, dried and concentrated to dryness to yield the compound of formula 5.

A solution of the compound of formula 5 and borane dimethylsulfide in THF is heated at reflux for from about 0.5 hour to about 4 hours. The solvent is removed and the residue is heated with mineral acid, preferably HCl for from about 5 minutes to about 2 hours. The cooled mixture is then neutralized with aqueous NaHCO$_3$ solution and extracted with a polar solvent, preferably EtOAc. The organic extract is dried, filtered and concentrated to dryness to yield the compound of formula 6.

A solution of n-butyl lithium in a nonpolar solvent such as, for instance, hexane is added to a stirred solution of the compound of formula 6 in THF at a lowered temperature, preferably −78° C. After stirring for from about 0.5 hour to about 4 hours, SO$_2$ is introduced over the surface of the reaction mixture for from a few minutes to about 1 hour. The reaction mixture is stirred about an additional ¼ hour at this temperature and allowed to warm to room temperature. The solvent is removed under reduced pressure and the residue is dissolved in a solution of NaOAc•3H$_2$O in H$_2$O at about 0° C. Hydroxylamine-O-sulfonic acid is added and the mixture is stirred overnight at about room temperature. The mixture is treated with a solution of saturated NaHCO$_3$, diluted with H$_2$O and extracted with EtOAc. The organic extracts are washed with brine, dried, filtered and concentrated to dryness to yield the compound of formula 7.

A solution of (NH$_4$)$_2$Ce(NO$_3$)$_6$ in H$_2$O is added to a solution of the compound of formula 7 in CH$_3$CN. After stirring for about 24 hours at about room temperature, the CH$_3$CN is removed under reduced pressure. The residue is diluted with H$_2$O, adjusted to pH 8–9 with aqueous NH$_3$ and extracted with EtOAc (3×). The organic extracts are washed with brine, dried, filtered and concentrated to dryness to yield the compound of formula 8.

Compounds of formula 7 and 8 wherein R$_5$ is other than H are prepared by adding lithium bis(trimethylsilyl)amide in hexane to a compound of formula 6 followed by addition of a compound of formula R$_5$X wherein R$_5$ has the meaning defined previously and X is halide, preferably iodide. The reaction mixture is allowed to warm to about room temperature and stirred overnight. The solvent is removed, preferably under reduced pressure, and the residue is taken up in H$_2$O and a polar solvent such as, for example, EtOAc. The extracts are washed with brine, dried, filtered and concentrated to dryness to yield the R$_5$ derivative. Treatment of this derivative according to the procedure of step G of example 1 yields the sulfonamide of formula 7. The p-methoxybenzyl group is removed following the procedure of example 2.

Compounds of formula 8 wherein R$_6$ is other than H are prepared by heating a compound of formula 8 with R$_6$COCl and borane dimethylsulfide in THF at reflux for from about 0.5 hour to about 4 hours. The solvent is removed and the residue is heated with mineral acid, preferably HCl for from about 5 minutes to about 2 hours. The cooled mixture is then neutralized with aqueous NaHCO$_3$ solution and extracted with a polar solvent, preferably EtOAc. The organic extract is dried, filtered and concentrated to dryness to yield the desired N-substituted compound.

The following examples illustrate the present invention without, however, limiting the same thereto. All temperatures are indicated in degrees Celsius.

EXAMPLE 1

3b,4,5,6,7,7a-Hexahydro-8H-4-(4-methoxybenzyl)-thieno[2,3-h][1,6]thiaquinoline-9,9-dioxide-2-sulfonamide (7)

A. Preparation of 2-(2-thiophenylthio)methyl-4-ethoxycarbonylbutyric acid (1)

Under N$_2$, a mixture of 2-methylene-4-ethoxycarbonylbutyric acid (17 g, 0.09 mol), triethylamine (4.3 g, 0.04 mol) in THF (120 ml) and 2-mercaptothiophene (11 g, 0.095 mol) was heated at reflux. After 24 hours the reaction mixture was cooled to room temperature and poured into 3N HCl (400 ml). The aqueous layer was extracted with EtOAc (3×) and the combined organic extracts were backwashed with saturated NaCl, dried, filtered and concentrated to dryness. The residue was chromatographed on a Still column and the product eluted with 15% $CH_3OH$-$CHCl_3$ saturated with $NH_3$ to yield 14 g of 1 wherein $R_1$, $R_2$, $R_3$ and $R_4$ are each H.

B. Preparation of 5,6-dihydro-4-oxo-5-(2-ethoxycarbonylethyl)thieno[2,3-b]thiopyran (2)

Under $N_2$, thionyl chloride (5.5 g, 0.043 mol) was added dropwise to a solution of 1 (11.5 g, 0.04 mol) in DMF (4 drops) and methylene chloride (100 ml). After the addition, the solution was stirred at room temperature for 4.5 hours. The mixture was then cooled to $-10°$ and $SnCl_4$ (5.3 g, 0.02 mol) was added dropwise. After the addition the reaction was allowed to stir at room temperature for 28 hours. The mixture was then added to $H_2O$ and the aqueous layer extracted with EtOAc (3×). The organic extracts were backwashed with saturated $NaHCO_3$, dried, filtered and concentrated to dryness to yield 10.5 g (97%) of 2 wherein $R_1$, $R_2$, $R_3$ and $R_4$ are each H.

C. Preparation of cis 5,6-dihydro-6-(2-ethoxycarbonylethyl)-4-(4-methoxybenzylamino)-4H-thieno[2,3-b]thiopyran (3)

To a solution of 2 (10.4 g, 0.039 mol) in THF (110 ml) and toluene (110 ml) at 0° is added 4-methoxybenzylamine (25.5 ml, 26.8 g, 0.195 mol). Titanium tetrachloride (2.2 ml, 3.8 g, 0.02 mol) is added to the cold solution and the resulting mixture is stirred for 0.75-1 hour. The mixture is added to a cold (0°) stirred suspension of $NaBH_4$ (4.5 g, 0.12 mol) in EtOH (900 ml). The resulting mixture is stirred for about 1 hour and acidified to pH 1 with 3N HCl. The solvent is removed in vacuo and the residue partitioned between EtOAc and saturated $NaHCO_3$ solution. The EtOAc layer is separated, dried and concentrated to dryness to yield 3 wherein $R_1$, $R_2$, $R_3$ and $R_4$ are each H.

D. Preparation of 3b,4,5,6,7,7a-hexahydro-5-oxo-8H-4-(4-methoxybenzyl)thieno[2,3-h][1,6]thiaquinoline (4)

A solution of $(CH_3)_3Al$ in toluene (23 ml, 2M, 0.046 mol) is added to a stirred solution of compound 3 (8.9 g, 0.023 mol) in toluene (575 ml) at 0° C. under $N_2$. The reaction mixture is brought to ambient temperature and then heated at reflux for 4 hours. The reaction mixture is cooled in an ice bath and treated with 3N HCl (100 ml) and diluted with $H_2O$ (500 ml) and EtOAc (500 ml). The layers are separated and the organic phase is washed with $H_2O$, brine, dried, and concentrated to dryness to yield 4 wherein $R_1$, $R_2$, $R_3$, and $R_4$ are each H.

E. Preparation of 3b,4,5,6,7,7a-hexahydro-5-oxo-8H-4-(4-methoxybenzyl)thieno[2,3-h][1,6]thiaquinoline-11,11-dioxide (5)

A solution of Oxone® (0.83 g, 0.0014 mol) in $H_2O$ (12 ml) is added to a stirred solution of 4 (0.15 g, 0.00045 mol) in $CH_3OH$ (6 ml). After stirring for 2 hours, the reaction mixture is extracted with EtOAc. The organic layer is washed with 10% aqueous sodium bisulfite solution, brine, dried and concentrated to dryness to yield 5 wherein $R_1$, $R_2$, $R_3$, and $R_4$ are each H.

F. Preparation of 3b,4,5,6,7,7a-hexahydro-4H-5-(4-methoxybenzyl)thieno[2,3-h][1,6]thiaquinoline-11,11-dioxide (6)

A solution of 5 (1.1 g, 0.0028 mol) and borane dimethylsulfide (0.84 ml, 10M in THF, 0.0084 mol) in THF (10 ml) is heated at reflux for 2 hours. The solvent is removed and the residue is heated with 6N HCl (10 ml) for 20 minutes. The cooled mixture is then neutralized with aqueous $NaHCO_3$ solution and extracted with EtOAc. The organic extract is dried, filtered and concentrated to dryness to yield 6 wherein $R_1$, $R_2$, $R_3$, and $R_4$ are each H.

G. Preparation of 3b,4,5,6,7,7a-hexahydro-8H-4-(4-methoxybenzyl)thieno[2,3-h][1,6]thiaquinoline-9,9-dioxide-2-sulfonamide (7)

A solution of n-butyl lithium in hexane (8 ml, 2.5M, 0.02 mol) is added to a stirred solution of 6 (6.2 g, 0.017 ml) in THF (150 ml) at $-78°$ C. After stirring for 2 hours, $SO_2$ is introduced over the surface of the reaction mixture for 20 minutes. The reaction mixture is stirred an additional ¼ hour at this temperature and allowed to warm to room temperature. The solvent is removed under reduced pressure and the residue is dissolved in a solution of $NaOAc•3H_2O$ (6.5 g, 0.048 mol) in $H_2O$ (60 ml) at 0° C. Hydroxylamine-O-sulfonic acid (4.6 g, 0.041 mol) is added and the mixture is stirred overnight at room temperature. The mixture is treated with a solution of saturated $NaHCO_3$ (50 ml), diluted with $H_2O$ (1500 ml) and extracted with EtOAc (3×). The organic extracts are washed with brine, dried, filtered and concentrated to dryness to yield 7 wherein $R_1$, $R_2$, $R_3$, and $R_4$ are each H.

EXAMPLE 2

Preparation of 3b,4,5,6,7,7a-hexahydro-8H-thieno[2,3-h][1,6]thiaquinoline-9,9-dioxide-2-sulfonamide (8)

A solution of $(NH_4)_2Ce(NO_3)_6$ (32.9 g, 0.06 mol) in $H_2O$ (80 ml) is added to a solution of 7 (5.3 g, 0.012 mol) in $CH_3CN$ (800 ml). After stirring for 24 hours at room temperature, the $CH_3CN$ is removed under reduced pressure. The residue is diluted with $H_2O$, adjusted to pH 8-9 with aqueous $NH_3$ and extracted with EtOAc (3×). The organic extracts are washed with brine, dried, filtered and concentrated to dryness to yield 8 wherein $R_1$, $R_2$, $R_3$, and $R_4$ are each H.

EXAMPLE 3

Preparation of 3b,4,5,6,7,7a-hexahydro-8H-8-methylthieno[2,3-h][1,6]thiaquinoline-9,9-dioxide-2-sulfonamide A solution of lithium bis(trimethylsilyl)amide in hexane (28 ml, 1M, 0.028 mol) is added dropwise to a stirred solution of 6 (8.3 g, 0.023 mol) in THF (200 ml) at $-78°$ C. When addition is complete, methyl iodide (6.5 g, 0.046 mol) is added at this temperature, then the reaction mixture is allowed to warm to room temperature and stirred overnight. The solvent is removed under reduced pressure and the residue is taken up in $H_2O$ (300 ml) and EtOAc (3×). The combined extracts are washed with brine, dried, filtered and concentrated to dryness to yield the title compound of formula 6 wherein $R_5$ is methyl.

Treatment of this compound as described in Example 1, Step G yields the corresponding compound of formula 7.

The p-methoxybenzyl group is removed as described in Example 2 by reaction with $(NH_4)_2Ce(NO_3)_6$ to the corresponding compound of formula 8.

EXAMPLE 4

Preparation of 3b,4,5,6,7,7a-hexahydro-8H-8-substituted thieno[2,3-h][1,6]thiaquinoline-9,9-dioxide-2-sulfonamide (12)

Utilizing the procedures as described in Example 3 the following compounds of formula 8 are prepared by substituting for methyl bromide a compound of formula $R_4Br$ wherein $R_4$ is

| $R_4$ |
|---|
| $CH_3-$ |
| $CH_3CH_2-$ |
| $CH_3CH_2CH_2-$ |
| $CH_3OCH_2CH_2CH_2-$ |
| $CH_3OCH_2CH_2OCH_2-$ |
| $CH_3OCH_2CH_2OCH_2CH_2-$ |
| $CH_3OCH_2CH_2OCH_2CH_2CH_2-$ |
| $CH_2=CHCH_2OCH_2-$ |
| $CH_2=CHCH_2-$ |

EXAMPLE 5

Preparation of 3b,4,5,6,7,7a-hexahydro-8H-4-isobutylthieno[2,3-h][1,6]thiaquinoline-9,9-dioxide-2-sulfonamide The title compound 13 is prepared as described in Example 1, steps A–G but substituting isobutylamine for 4-methoxybenzylamine.

EXAMPLE 6

Preparation of 3b,4,5,6,7,7b-hexahydro-8H-4-substituted-8-substituted thieno[2,3-h][1,6]thiaquinoline-9,9-dioxide-2-sulfonamides Compounds 14 are prepared as described in Examples 1–5 but substituting the appropriate reagents where necessary.

| $R_6$ | $R^5$ |
|---|---|
| $(CH_3)_2CHCH_2-$ | $CH_3-$ |
| $CH_3CH_2CH_2$ | $CH_3CH_2-$ |
| $CH_3CH_2-$ | $CH_3CH_2CH_2-$ |
| $CH_3CH_2-$ | $CH_3OCH_2CH_2CH_2-$ |
| | $CH_2=CHCH_2-$ |
| 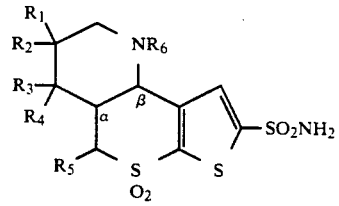 | $CH_2$ |
| H | $CH_2=CHCH_2OCH_2-$ |
| H | $CH_3OCH_2CH_2CH_2-$ |
| H | $CH_3-$ |
| H | $CH_3CH_2-$ |
| H | $CH_3CH_2CH_2-$ |
| H | $CH_3OCH_2-$ |
| H | $CH_3OCH_2CH_2-$ |
| H | $CH_3OCH_2CH_2CH_2OCH_2CH_2CH_2-$ |
| H | $CH_3OCH_2CH_2OCH_2CH_2-$ |
| H | $CH_3OCH_2CH_2NHCH_2-$ |
| H | $HOCH_2CH_2CH_2-$ |
| H | $CH_3S(O)_mCH_2CH_2OCH_2-$ |
| H | $CH_3OCH_2CH_2S(O)CH_2-$ |
| H | $HOCH_2CH_2S(O)_mCHCHCH_2-$ |
| H | $CH_3S(O)_mCH_2CH_2S(O)_mCH_2-$ |

What is claimed is:

1. A compound of the formula

having a cis configuration at the α- and β-carbons, the enantiomers and mixtures thereof, or an ophthalmologically acceptable salt thereof wherein $R_1$, $R_2$, $R_3$, $R_4$, and $R_6$ are independently H or straight or branched chain lower alkyl; $R_5$ is H, lower alkyl, lower alkenyl or lower alkyl substituted by hydroxy, alkoxy, hydroxyalkoxy, alkoxyalkoxy, hydroxyalkoxyalkoxy, alkylamino, hydroxyalkylamino, alkoxyalkylamino, hydroxyalkoxyalkylamino, alkyl-$S(O)_m$, hydroxyalkyl-$S(O)_m$, alkoxyalkyl-$S(O)_m$, hydroxyalkoxyalkyl-$S(O)_m$, alkyl-$S(O)_m$alkyoxy, hydroxyalkyl-$S(O)_m$alkyoxy, alkyl-$S(O)_m$alkyl-$S(O)_m$ and hydroxyalkyl-$S(O)_m$alkyl-$S(O)_m$; and m is 0, 1 or 2.

2. A compound according to claim 1 wherein $R_1$, $R_2$, $R_3$, $R_4$, and $R_6$ are H or straight or branched chain $C_{1-6}$alkyl, $R_5$ is 1) H or lower alkyl, preferably $C_{1-6}$;
2) $C_{1-6}$ alkyl substituted with
   a) hydroxy,
   b) $C_{1-3}$alkyl—O—,
   c) hydroxy$C_{1-3}$alkyl—O—,
   d) $C_{1-3}$alkyl—O—$C_{1-3}$alkyl—O—,
   e) hydroxy$C_{1-3}$alkyl—O—$C_{1-3}$alkyl—O—,
   f) $C_{1-3}$alkyl—NH—,
   g) hydroxy$C_{1-3}$alkyl—NH—,
   h) $C_{1-3}$alkyl—O—$C_{1-3}$alkyl—NH—,
   i) hydroxy$C_{1-3}$alkyl—O—$C_{1-3}$alkyl—NH—,
   j) $C_{1-3}$alkyl—$S(O)_m$—,
   k) hydroxy$C_{1-3}$alkyl—$S(O)_m$—,
   l) $C_{1-3}$alkyl—O—$C_{1-3}$alkyl—$S(O)_m$—,
   m) hydroxy$C_{1-3}$alkyl—O—$C_{1-3}$alkyl—$S(O)_m$—,
   n) $C_{1-3}$alkyl—$S(O)_m$—$C_{1-3}$alkyl—O—,
   o) hydroxy$C_{1-3}$alkyl—$S(O)_m$—$C_{1-3}$alkyl—O—,
   p) $C_{1-3}$alkyl—$S(O)_m$—$C_{1-3}$alkyl—$S(O)_m$,
   q) hydroxy$C_{1-3}$alkyl—$S(O)_m$—$C_{1-3}$alkyl—$S(O)_m$—;
3) $C_{2-6}$alkenyl;

and m is independently 0, 1 or 2.

3. A compound according to claim 2 wherein $R_1$, $R_2$, $R_3$, $R_4$, and $R_6$ are independently H or $C_{1-6}$alkyl, and $R_5$ is H, $C_{1-6}$alkyl or $C_{1-6}$alkyl substituted by hydroxy, alkoxy, hydroxyalkoxy, alkoxyalkoxy, alkylamino, alkoxyalkylamino, alkyl—$S(O)_m$—, hydroxy$C_{1-3}$alkyl—$S(O)_m$—, $C_{1-3}$alkyl—$S(O)_m$—$C_{1-3}$alkyl—$S(O)_m$—, $C_{1-3}$alkyl—O—$C_{1-3}$alkyl—$S(O)_m$—, $C_{1-3}$alkyl—$S(O)_m$—$C_{1-3}$alkyl—O—, or $C_{2-6}$alkenyl, and m is independently 0, 1 or 2.

4. A composition for the treatment of ocular hypertension comprising an ophthalmologically acceptable carrier and an effective ocular antihypertensive amount of a compound of claim 1.

5. A method of treating elevated intraocular pressure comprising the topical administration to a member of a mammalian species in need of such treatment of an effective intraocular pressure lowering amount of a compound of claim 1.